United States Patent
Seyer et al.

(10) Patent No.: US 7,344,565 B2
(45) Date of Patent: Mar. 18, 2008

(54) ACETABULAR COMPONENT INSERTION AND EXTRACTION TOOL FOR USE THEREWITH, AND METHOD OF LOCKING AN ACETABULAR COMPONENT TO AN INSERTION AND EXTRACTION TOOL

(75) Inventors: Steven F. Seyer, Germantown, TN (US); Ramon Luna, Memphis, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 454 days.

(21) Appl. No.: 10/772,128

(22) Filed: Feb. 4, 2004

(65) Prior Publication Data

US 2004/0186586 A1 Sep. 23, 2004

Related U.S. Application Data

(60) Provisional application No. 60/444,689, filed on Feb. 4, 2003.

(51) Int. Cl.
*A61F 2/34* (2006.01)

(52) U.S. Cl. .................. 623/22.21; 606/99; 623/22.12

(58) Field of Classification Search .. 623/22.11–22.39, 623/19.11–19.14; 606/81, 91, 99
See application file for complete search history.

(56) References Cited

U.S. PATENT DOCUMENTS

| | | | | |
|---|---|---|---|---|
| 3,683,421 A | * | 8/1972 | Martinie | 623/22.13 |
| 3,864,758 A | * | 2/1975 | Yakich | 623/22.13 |
| 3,869,730 A | * | 3/1975 | Skobel | 623/19.12 |
| 3,903,549 A | * | 9/1975 | Deyerle | 623/22.36 |
| RE28,895 E | * | 7/1976 | Noiles | 623/22.31 |
| 4,023,572 A | * | 5/1977 | Weigand et al. | 606/81 |
| 4,770,661 A | * | 9/1988 | Oh | 623/22.2 |
| 4,883,491 A | * | 11/1989 | Mallory et al. | 623/22.31 |
| 5,021,062 A | * | 6/1991 | Adrey et al. | 623/22.36 |
| 5,098,437 A | * | 3/1992 | Kashuba et al. | 606/89 |
| 5,108,447 A | * | 4/1992 | Zeiler et al. | 623/22.14 |
| 5,133,771 A | * | 7/1992 | Duncan et al. | 623/23.2 |
| 5,190,550 A | * | 3/1993 | Miller et al. | 606/85 |
| 5,192,329 A | * | 3/1993 | Christie et al. | 623/22.22 |
| 5,314,487 A | * | 5/1994 | Schryver et al. | 623/22.37 |
| 5,314,491 A | * | 5/1994 | Thongpreda et al. | 623/22.29 |
| 5,358,532 A | * | 10/1994 | Evans et al. | 623/22.23 |
| 5,417,696 A | * | 5/1995 | Kashuba et al. | 606/91 |
| 5,458,650 A | * | 10/1995 | Carret et al. | 623/22.25 |
| 5,486,181 A | * | 1/1996 | Cohen et al. | 606/91 |
| 5,507,825 A | * | 4/1996 | Frei | 623/22.36 |
| 5,549,691 A | * | 8/1996 | Harwin | 623/22.37 |

(Continued)

*Primary Examiner*—Corrine McDermott
*Assistant Examiner*—Ann Schillinger (57) ABSTRACT

An acetabular component comprises a thin-walled, partial spherical body having an inner surface defining an articular surface and having angled recesses along an outer surface of the body for releasable engagement with an insertion and extraction tool. An insertion and extraction tool comprises a spring-loaded locking member movable from an extended position to a retracted position in response to relative sliding movement of an outer sleeve and inner shaft of the tool effected via an actuating force at a proximal end of the tool. The tool comprises engagement members insertable in the recesses when the locking member is retracted and, upon release of the actuating force, the locking member automatically returns to the extended position causing fingers of the locking members to enter the recesses and lock the acetabular cup to the tool.

14 Claims, 10 Drawing Sheets

U.S. PATENT DOCUMENTS

| | | | |
|---|---|---|---|
| 5,571,200 A * | 11/1996 | Cohen et al. | 623/22.12 |
| 5,658,294 A * | 8/1997 | Sederholm | 606/91 |
| 5,702,473 A * | 12/1997 | Albrektsson et al. | 623/22.31 |
| 5,732,992 A * | 3/1998 | Mauldin | 294/119.1 |
| 5,800,558 A * | 9/1998 | LaHaise, Sr. | 623/22.2 |
| 5,885,299 A * | 3/1999 | Winslow et al. | 606/99 |
| 5,904,688 A * | 5/1999 | Gilbert et al. | 606/86 |
| 5,928,287 A * | 7/1999 | Keller | 623/22.21 |
| 5,938,701 A * | 8/1999 | Hiernard et al. | 606/99 |
| 5,951,605 A * | 9/1999 | Dennis et al. | 623/13.11 |
| 5,989,294 A * | 11/1999 | Marlow | 623/22.16 |
| 6,022,357 A * | 2/2000 | Reu et al. | 606/99 |
| 6,063,124 A * | 5/2000 | Amstutz | 623/22.21 |
| 6,132,469 A * | 10/2000 | Schroeder | 623/22.24 |
| 6,152,961 A * | 11/2000 | Ostiguy et al. | 623/22.28 |
| 6,162,256 A * | 12/2000 | Ostiguy et al. | 623/22.26 |
| 6,168,600 B1 * | 1/2001 | Grace et al. | 606/81 |
| 6,228,121 B1 * | 5/2001 | Khalili | 623/22.36 |
| 6,238,435 B1 * | 5/2001 | Meulink et al. | 623/22.12 |
| 6,281,264 B1 * | 8/2001 | Salovey et al. | 523/115 |
| 6,432,141 B1 * | 8/2002 | Stocks et al. | 623/22.13 |
| 6,451,058 B2 * | 9/2002 | Tuke et al. | 623/22.21 |
| 6,488,713 B1 * | 12/2002 | Hershberger | 623/22.11 |
| 6,589,284 B1 * | 7/2003 | Silberer | 623/22.29 |
| 6,916,342 B2 * | 7/2005 | Frederick et al. | 623/22.29 |
| 7,022,141 B2 * | 4/2006 | Dwyer et al. | 623/22.12 |
| 2001/0051830 A1 * | 12/2001 | Tuke et al. | 623/22.12 |
| 2002/0040245 A1 * | 4/2002 | Lester et al. | 623/22.23 |
| 2005/0187637 A1 * | 8/2005 | Karrer et al. | 623/22.24 |

\* cited by examiner

FIG.29
DETAIL H

FIG.30
SECTION I-I

ACETABULAR COMPONENT INSERTION AND EXTRACTION TOOL FOR USE THEREWITH, AND METHOD OF LOCKING AN ACETABULAR COMPONENT TO AN INSERTION AND EXTRACTION TOOL

RELATED APPLICATIONS

This application claims priority to U.S. Provisional Patent Application Ser. No. 60/444,689, filed Feb. 4, 2003.

BACKGROUND OF THE INVENTION

1. Field of the Invention

The present invention relates generally to insertion and extraction of prosthetic acetabular components and, more particularly, to prosthetic acetabular components, to insertion and extraction tools for releasable locking engagement with prosthetic acetabular components and to methods of locking prosthetic acetabular components to insertion and extraction tools.

2. Brief Discussion of the Related Art

Many surgical procedures involve the implantation of prosthetic components on prepared bone surfaces, particularly the bone surfaces of anatomical joints. In the area of hip surgery, prosthetic acetabular components are commonly implanted on prepared bone surfaces of the acetabulum to provide a socket for articular engagement with a head at the upper end of the femur. Prosthetic acetabular components typically have a partial spherical configuration, and preparation of the acetabulum to receive an acetabular component generally involves the formation of a cavity in the bone to receive the partial spherical configuration. Ordinarily, it is desirable that the cavity in the bone be no larger than necessary to accommodate the acetabular component so as to preserve as much natural bone as possible. It is also desirable that the thickness of the partial spherical wall of the acetabular component be no thicker than necessary in order to minimize the size of the cavity required to be formed in the bone for a given size articular surface area.

Insertion of prosthetic acetabular components in the prepared bone cavities often necessitates the application of significant impaction forces on the acetabular components, especially where the components are designed to be jam or interference fitted in the bone cavities. Prior to fixation of the acetabular components in the bone cavities, the position of the acetabular components in the cavities may have to be adjusted in order to establish optimal fit and orientation of the acetabular components with the head at the upper end of the femur. Adjustment may involve moving the acetabular components relative to the bone cavities until correct positioning is achieved. In order to enhance the efficiency of the surgical procedures, it is desirable for adjustment to be effected while the acetabular components remain within or close to the bone cavities without having to be withdrawn from the patients' bodies. Extraction of acetabular components from the bone cavities after being fixated to the bone typically requires that vigorous extraction forces be applied to the acetabular components since the extraction forces must be strong enough to overcome the fixation by which the acetabular components are fixated in the bone cavities.

Various tools have been proposed for mechanically engaging acetabular components for insertion in and/or extraction from bone cavities as represented by U.S. Pat. No. 5,037,424 to Aboczsky, U.S. Pat. No. 5,169,399 to Ryland et al, U.S. Pat. No. 5,250,051 to Maryan, U.S. Pat. No. 5,417,696 to Kashuba et al, U.S. Pat. No. 5,486,181 to Cohen et al, U.S. Pat. No. 5,540,697 to Rehmann et al, U.S. Pat. No. 5,658,294 to Sederholm, U.S. Pat. No. 5,683,399 to Jones, U.S. Pat. No. 5,904,688 to Gilbert et al and U.S. Pat. No. 6,063,124 to Amstutz, and by U.S. patent application Publication No. 2002/0177854 A1 to Tuke et al. Prior tools are not self-locking with the acetabular components and require complicated structure and operating steps in order to effect locking of the acetabular components to the tools. The mechanical lock between the acetabular components and prior tools may not be strong enough for the applied impaction and/or extraction forces so that damage may occur to the acetabular components and/or the tools. Prior tools may become loose from the acetabular components as a result of vibration and/or twisting. Where permanent locking structure is provided on the inner surfaces of the acetabular components, the locking structure may interfere with or detract from the articular surface. Moreover, locking structure on the inner surfaces may detrimentally interfere with the femoral head in articular engagement with the socket of the acetabular component.

The Gilbert et al patent discloses an insertion tool including a body having a plurality of L-shaped fingers for being introduced in corresponding notches in a thick-walled acetabular cup and then rotated to engage undercut walls of the notches. A projection is thereafter insertable into the portion of only one of the notches which is unoccupied by the corresponding finger to prevent rotation of the body relative to the acetabular cup. In order to insert the projection in and withdraw the projection from the unoccupied portion of the notch, a finger grip that is separate from the handle of the tool must be manually moved axially and rotatably to effect extension and retraction of the projection. Accordingly, the tool is not self-locking with the acetabular cup but, rather, requires a series of complicated manipulations to effect locking and unlocking. The finger grip is inconveniently located remote from the gripping knob of the handle, thusly requiring two-handed operation. Only one projection and finger grip are provided, such that the weight of the locking structure and finger grip are not distributed evenly about the longitudinal axis of the tool. The resulting weight imbalance impairs the surgeon's ability to manipulate the tool with ease and accuracy via the handle. The tool does not have a centering device to facilitate axial alignment of the tool with the acetabular cup when introducing the fingers in the notches.

The Tuke et al patent relates to an impactor having a cable threaded through a corresponding acetabular cup and/or a removable cover for the acetabular cup, with the cable being looped over arms or mooring pegs of the impactor. Regardless of whether the cable is threaded prior to or during surgery, the threading procedure is tedious and labor intensive. It is possible for the cable to become caught on anatomical structure or other instruments at the surgical site, thereby complicating the surgical procedure. In order to effect locking of the acetabular cup to the impactor via the cable, the cable is tensioned by advancing a carriage of the impactor via manual rotation of a knob. Significant mechanical effort is needed to obtain minimal advancement of the carriage and adds to the time required to complete the surgical procedure. Once the impactor is disconnected from the acetabular cup following implantation, the cable must be cut and removed from the patient's body. The patient is therefore placed at risk since the cable could be accidentally dropped inside the patient's body and/or left in the patient's body inadvertently. Extraction using the tool is not feasible.

The acetabular cup disclosed in the Amstutz patent has recesses within its peripheral rim for engagement with fingers of a bayonet coupler of an impactor and/or extractor tool. The acetabular cup must be moved away from the bayonet coupler by a securing member of the tool in order to lock the fingers in the recesses. The recesses are enclosed between the inner and outer surfaces of the partial spherical wall of the acetabular cup, thereby requiring a thicker wall and a larger size cavity in the acetabulum.

SUMMARY OF THE INVENTION

Accordingly, it is a primary object of the present invention to overcome the aforementioned disadvantages of prior acetabular components, insertion and/or extraction tools for use therewith, and methods of locking acetabular components to such tools.

Another object of the present invention is to ensure automatic self-locking of an insertion and extraction tool with an acetabular component.

A further object of the present invention is to utilize spring-loaded locking arms in an insertion and extraction tool to establish a releasable lock with an acetabular component.

It is also an object of the present invention to facilitate alignment of an insertion and extraction tool with an acetabular component when inserting engagement protrusions of the tool in recesses of the acetabular component.

The present invention also has as an object to structurally and procedurally simplify insertion and extraction of prosthetic acetabular components.

These and other objects, advantages and benefits are realized with the present invention as generally characterized in an acetabular component and an insertion and extraction tool for use with the acetabular component. The acetabular component comprises a thin-walled, partial spherical body having a peripheral surface circumscribing a cavity, a plurality of recesses along the outer surface of the body each having an entry portion open along the peripheral surface and leading into an engagement portion angled from the entry portion. Each of the engagement portions has a first end aligned with the entry portion and a second end extending lengthwise beyond the entry portion to define a shoulder between the second end and the peripheral surface.

The insertion and extraction tool comprises an outer sleeve, an inner shaft longitudinally, slidably disposed in the outer sleeve and a spring biasing the outer sleeve and inner shaft longitudinally relative to one another. The outer sleeve has a distal end coupled with a locking member including a plurality of radially extending arms and a locking finger extending longitudinally, distally from each arm. The inner shaft has a distal end carrying an engagement plate disposed distally of the distal end of the outer sleeve. The engagement plate has a plurality of engagement protrusions at locations corresponding to the locations of the entry portions of the recesses. Each of the engagement protrusions has a leg extending longitudinally, distally from the engagement plate to a foot angled from and extending lengthwise beyond the leg. The engagement plate includes a plurality of channels therein slidably receiving the arms of the locking member, respectively. The spring biases the outer sleeve and the inner shaft longitudinally relative to one another to a locked position for the insertion and extraction tool in which the locking member is in an extended position relative to the engagement plate. In the extended position, the locking fingers of the locking member protrude distally beyond the engagement plate alongside the legs of the engagement protrusions. The insertion and extraction tool is movable to an unlocked position in response to an actuating force applied to the tool to effect relative longitudinal movement of the outer sleeve and inner shaft to move the locking member to a retracted position relative to the engagement plate. In the retracted position for the locking member, the locking fingers are retracted within the channels of the engagement plate, allowing the feet of the engagement protrusions to be inserted through the entry portions of the recesses into the first ends of the engagement portions of the recesses. The feet are movable into the second ends of the engagement portions in response to rotation of the engagement plate about its central longitudinal axis and, in this position, the shoulders of the acetabular component prevent withdrawal of the engagement protrusions from the recesses in a longitudinal direction. Each recess presents a portion unoccupied by the engagement protrusions when the feet are disposed in the second ends of the engagement portions of the recesses, respectively, and each entry portion has an opening along the peripheral surface of the acetabular component leading into the corresponding unoccupied portion. The tool is returned automatically to the locked position by the spring in response to removal of the actuating force, causing the locking member to be automatically returned to its extended position. In response to movement of the locking member to its extended position, the locking fingers enter the unoccupied portions of the recesses and prevent rotation of the engagement plate about its central longitudinal axis, such that the acetabular component is locked to the tool for use in inserting or extracting the acetabular component. An alignment or centering member may be disposed on the engagement plate for insertion in the cavity of the acetabular component to facilitate alignment of the feet with the entry portions of the recesses.

A method of locking an acetabular component to an insertion and extraction tool according to the present invention involves locking the acetabular component to the tool automatically in response to spring-loaded relative longitudinal sliding movement of an outer sleeve and inner shaft of the tool obtained when an actuating force is removed from a proximal end of the tool.

DESCRIPTION OF THE PREFERRED EMBODIMENTS

An acetabular component 10 according to the present invention is shown in FIGS. 1-6 and comprises a thin-walled, partial spherical body 12 having a peripheral end surface 14 circumscribing a cavity 16. The acetabular component 10 may be a one-piece acetabular cup in which the cavity thereof receives a femoral head or may be part of a multi-piece acetabular cup in which the component 10 is a shell for receiving a liner in cavity 16. Preferably, the acetabular component 10 is designed for articular engagement with a prosthetic femoral head, with the inner surface of the body 12 being made of superfinished cobalt chrome for metal-to-metal contact with the femoral head. The body 12 may be flattened at its apex as shown by surface 17. The peripheral end surface 14 is joined to a rim 18 of body 12 by an outer circumferential peripheral edge 19, and the rim 18 protrudes outwardly along the outer surface of the body. It is preferred that the outer surface, except for rim 18, comprise a porous or rough coating to promote bone ingrowth or on-growth, and the coating could also be eliminated from surface 17. Body 12 is thin-walled, having a wall thickness of about 3-6 mm in one embodiment. A plurality of L-shaped recesses 20 are formed in body 12 along its outer surface, the body 12 having three recesses 20 at equally spaced radial locations about a central axis of body 12. Each recess 20 comprises an entry portion 22 extending from the peripheral surface 14 in the direction of the apex to an engagement portion 24 extending parallel to outer peripheral edge 19. The entry portions 22 present openings into the recesses along peripheral surface 14. The engagement portions 24 have side edges 25, respectively, parallel to edge 19 and slightly beyond rim 18 in the direction of the apex. Each entry portion 22 is aligned with a first end of the corresponding engagement portion 24 while a second end of the engagement portion extends lengthwise beyond the entry portion. The second ends of the engagement portions 24 are separated from the peripheral surface 14 by shoulders 26, respectively, of the acetabular component. The recesses 20 are open along the peripheral end surface and the outer surface of body 12, and the body 12 being thin-walled minimizes the size of the cavity required to be formed in the acetabulum for a body of given articular surface area. The length of the engagement portions 24 is of a size to simultaneously receive the foot of an engagement protrusion and a locking finger of a locking member of an insertion and extraction tool as explained below.

Figure 1:
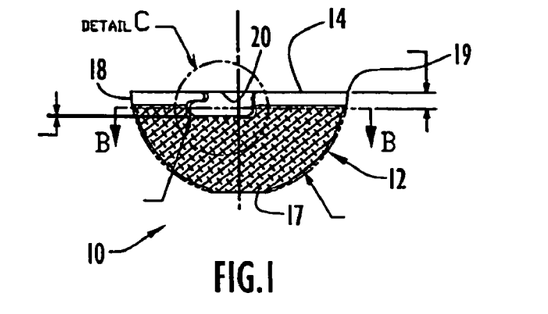
FIG. 1 is a side view of an acetabular component according to the present invention.
Figure 2:
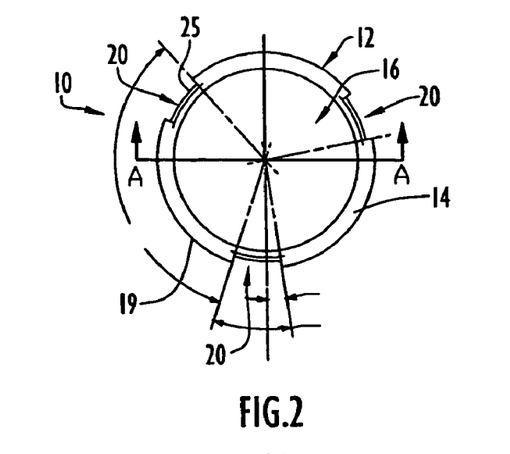
FIG. 2 is a top view of the acetabular component.
Figure 3:
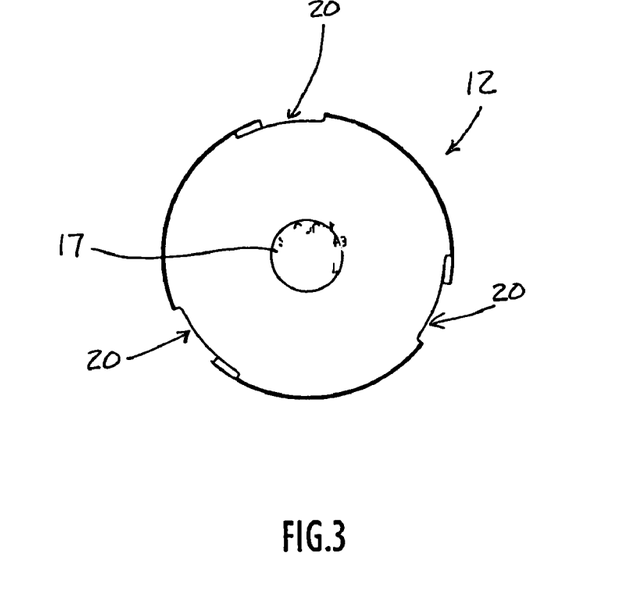
FIG. 3 is a bottom view of the acetabular component.
Figure 4:
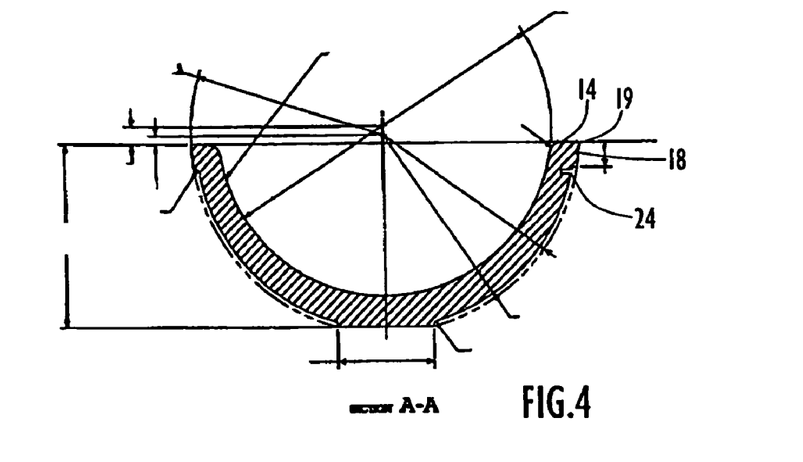
FIG. 4 is a sectional view taken along line A-A of FIG. 2.
Figure 5:
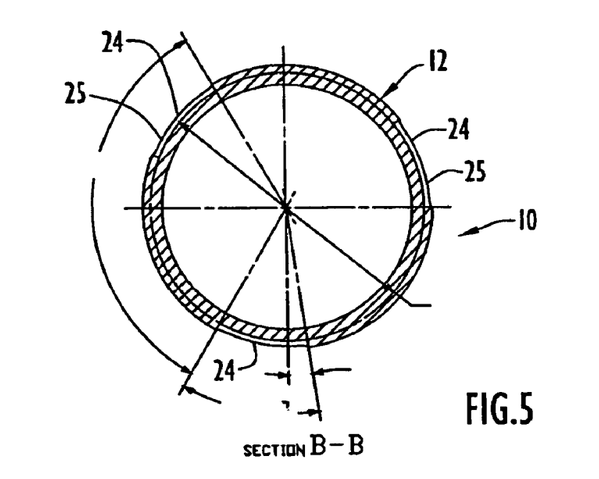
FIG. 5 is a sectional view taken along line B-B of FIG. 1.
Figure 6:
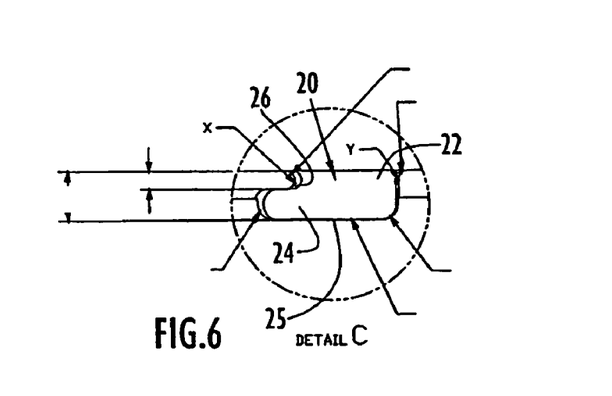
FIG. 6 is an enlarged fragmentary view of detail C of FIG. 1.
Figure 7:
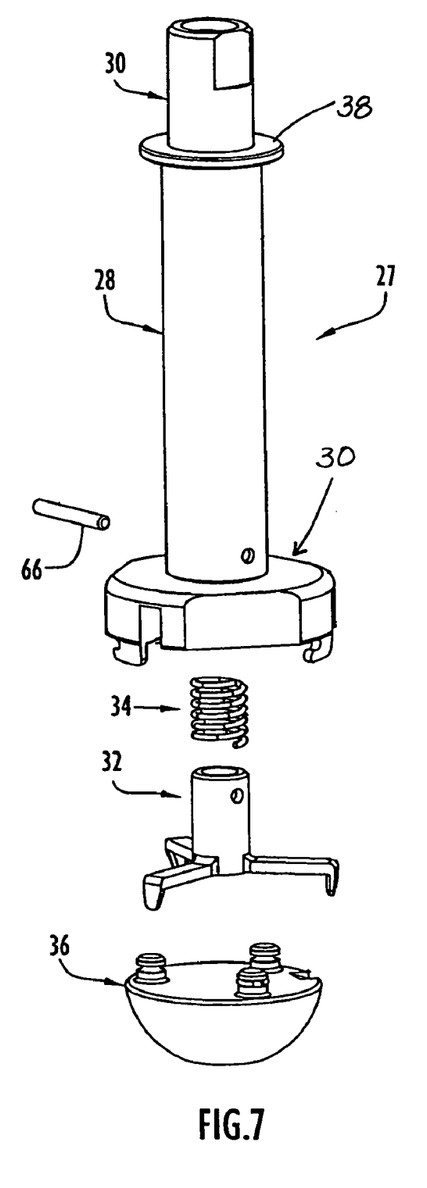
FIG. 7 is a partially exploded perspective view of an insertion and extraction tool according to the present invention.
Figure 8:
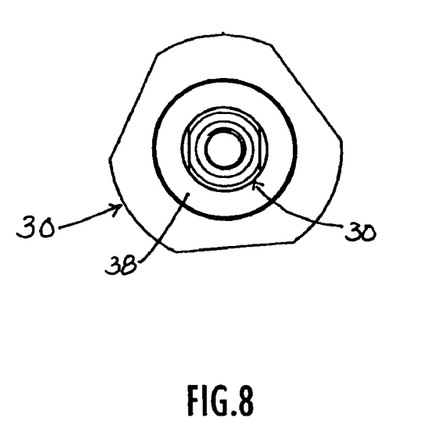
FIG. 8 is an end or top view of the insertion and extraction tool.
Figure 9:
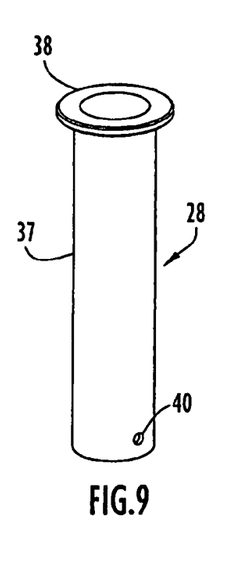
FIG. 9 is a perspective view of an outer sleeve of the insertion and extraction tool.
Figure 10:
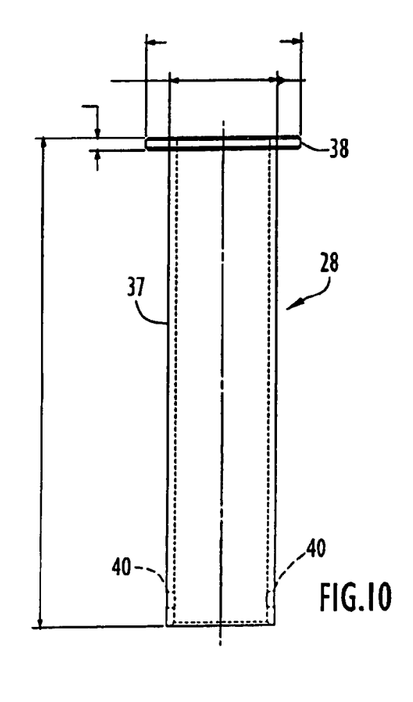
FIG. 10 is a side view of the outer sleeve.
Figure 11:
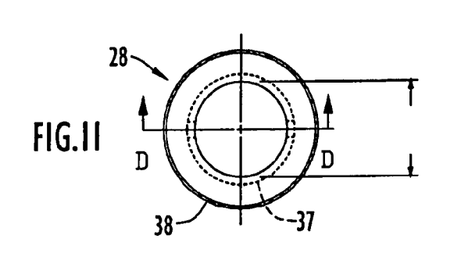
FIG. 11 is a top view of the outer sleeve.
Figure 12:
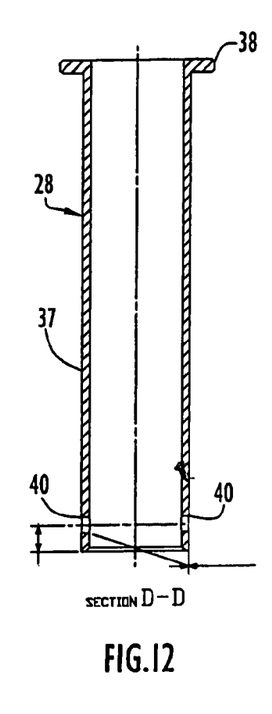
FIG. 12 is a sectional view taken along line D-D of FIG. 11.
Figures 13, 15:
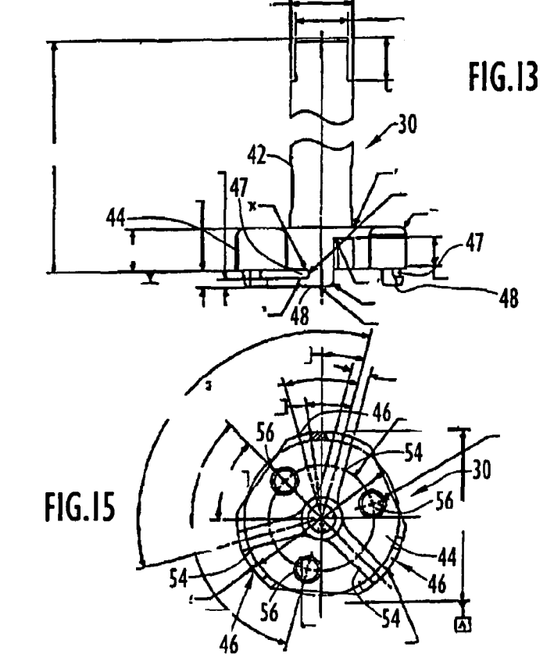
FIG. 13 is a broken side view of an engagement member of the insertion and extraction tool.
FIG. 15 is a bottom view of the engagement member.
Figure 14:
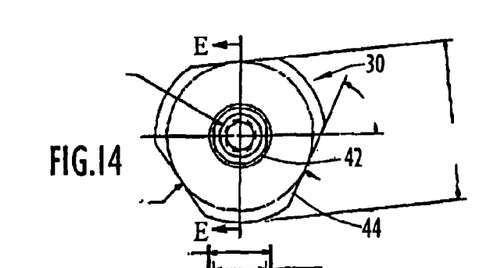
FIG. 14 is a top view of the engagement member.
Figure 16:
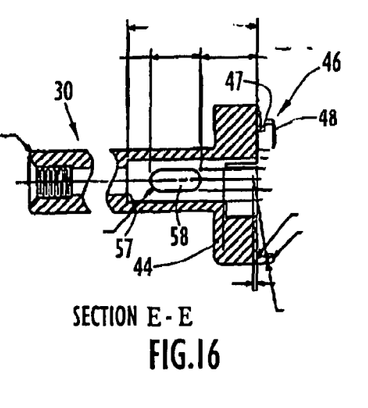
FIG. 16 is a broken sectional view taken along line E-E of FIG. 14.
Figures 17, 18, 21:
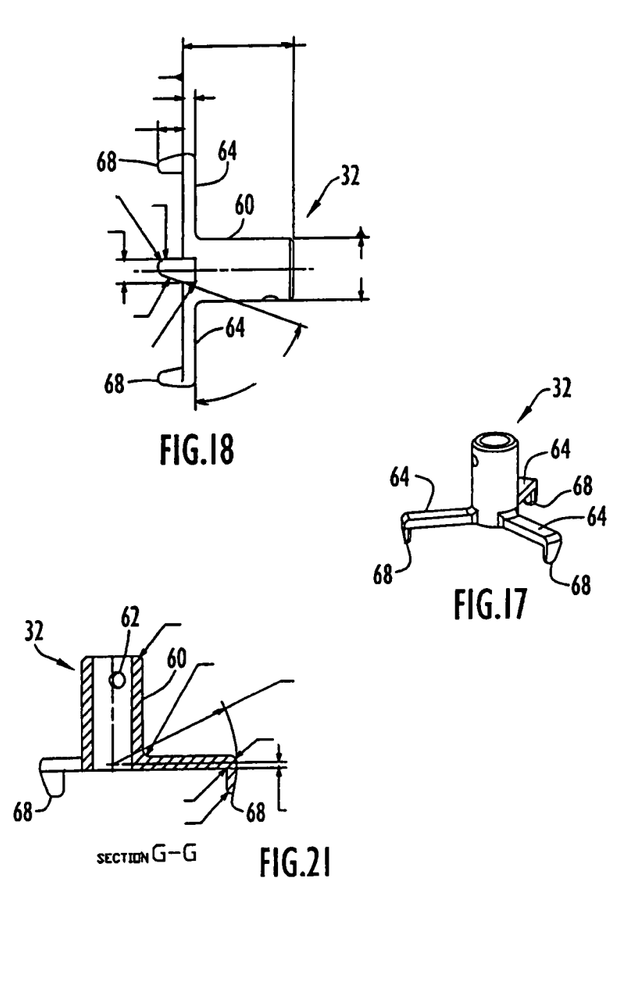
FIG. 17 is a perspective view of a locking member of the insertion and extraction tool.
FIG. 18 is a side view of the locking member.
FIG. 21 is a partial sectional view taken along line G-G of FIG. 19.
Figure 19:
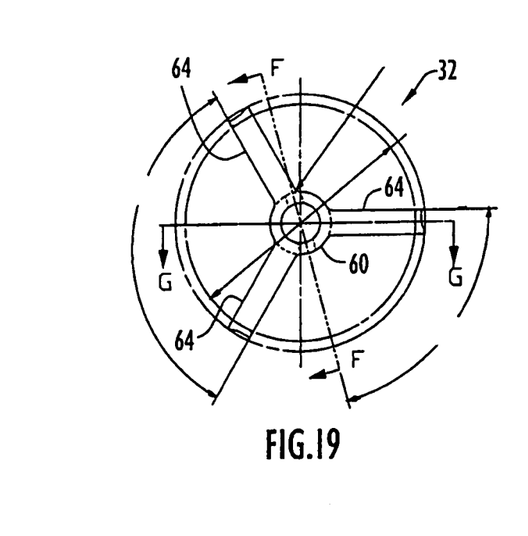
FIG. 19 is a bottom view of the locking member.
Figure 20:
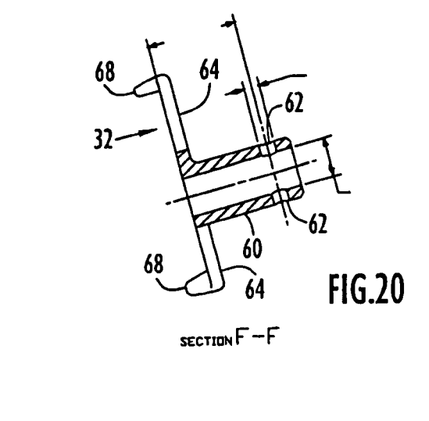
FIG. 20 is a partial sectional view taken along line F-F of FIG. 19.

The insertion and extraction tool 27 is shown in FIGS. 7 and 8 and comprises an outer member 28, an engagement member 30, a locking member 32, a spring 34 and an alignment or centering member 36. The outer member 28 is shown in FIGS. 9-12 and comprises a hollow cylindrical outer sleeve 37 having a protruding flange 38 at its proximal end and a pair of diametrically aligned holes 40 close to its distal end.

The engagement member 30 is depicted in FIGS. 13-16 and comprises a hollow inner shaft 42 slidably disposed within sleeve 37 and an engagement plate 44 at a distal end of shaft 42. The shaft 42 has a length such that engagement plate 44 is disposed distally of the distal end of outer sleeve 37 with a proximal end of shaft 42 disposed proximally of the proximal end of sleeve 37. The proximal ends of shaft 42 and sleeve 37 cooperate to form an actuator for the locking mechanism of the insertion and extraction tool. The proximal end of shaft 42 may be internally threaded for connection with other components such as a handle and/or a slap hammer. The engagement plate 44 has a peripheral configuration comprising equally spaced arcuate peripheral segments and straight peripheral segments between the arcuate peripheral segments. The arcuate peripheral segments are circumferential segments of a circle having its center aligned with the central longitudinal axis of the engagement member, and this circle corresponds or substantially corresponds to peripheral edge 19 of the acetabular component. The engagement plate 44 has a planar distal face which may abut the peripheral surface 14 when the acetabular component 10 is locked onto the insertion and extraction tool as described below.

A plurality of L-shaped engagement protrusions 46 extend from the distal face of engagement plate 44 along the arcuate peripheral segments, there being one engagement protrusion 46 for each recess 20 in the acetabular component 10. The engagement protrusions 46 are located at equally spaced radial locations about the central longitudinal axis of the engagement member corresponding to the locations of recesses 20. Each engagement protrusion comprises a leg 47 extending longitudinally, distally from the distal face to an engagement foot 48 extending lengthwise from the leg parallel to the arcuate peripheral segments. Each leg 47 is aligned with a first end of the corresponding foot 48, with a second end of the foot extending lengthwise beyond the leg. The feet 48 have a length longer than the dimension of legs 47 in the direction parallel to the arcuate peripheral segments. The length of feet 48 is selected to fit within the entry portions 22 of recesses 20 for positioning within the first ends of engagement portions 24 when the engagement plate 44 is moved toward the acetabular component 10 with the central longitudinal axis of the engagement member 30 axially aligned with the central axis of body 12. The distance between the distal edges of the engagement feet 48 and the distal face may be selected such that the distal face abuts the peripheral surface 14 when the distal edges of feet 48 abut the side edges 25 of the engagement portions 24. When the engagement protrusions 46 are thereafter rotated relative to the acetabular component 10 by rotating the engagement member about its central longitudinal axis in the direction of the second ends of the engagement portions 24, the second ends of feet 48 will be moved into the second ends of the engagement portions 24. The shoulders 26 will be disposed between the engagement plate 44 and the second ends of feet 48 such that the engagement protrusions 46 are prevented from being withdrawn from the acetabular component 10 in the axial or longitudinal direction. The legs 47 will be in abutment with the shoulders 26, with part of the first ends of engagement portions 24 and part of the entry portions 22 being unoccupied for reception of a locking finger of the locking member 32 into the recesses 20. Slots or channels 54 are formed in engagement plate 44 at equally spaced radial locations and open on the distal face thereof for slidably receiving arms of the locking member 32. The slots 54 have a depth to permit retraction and extension of the arms longitudinally as explained below. Holes 56 are formed in the engagement plate along the distal face thereof for releasable engagement with bosses of the alignment member 36. The shaft 42 has an internal ledge 57, and diametrically opposed channels or slots 58 are formed through the wall of shaft 42. The channels 58 are located between the ledge 57 and the engagement plate 44. The channels 58 extend in a longitudinal direction to permit relative sliding movement between the inner shaft 42 and the outer sleeve 37 as described below.

The locking member 32 is shown in FIGS. 17-20 and comprises a tubular stem 60 having a pair of diametrically aligned apertures 62 near its proximal end and having a plurality of radially extending arms 64 at its distal end. The stem 60 is slidably received in the inner shaft 42 of the engagement member 30 with the apertures 62, channels 58 and holes 40 aligned with one another, and a pin 66 is inserted therethrough with opposite ends of the pin secured to outer sleeve 37. Accordingly, the locking member 32 is fixedly secured to the outer sleeve 37 and is movable therewith as the shaft 42 of the engagement member 30 and the outer sleeve 37 are moved longitudinally relative to one another as permitted by the pin 66 moving in channels 58. The arms 64 are slidably disposed in the slots 54 of the engagement plate 44, and locking fingers or tabs 68 (designated 168 in the embodiment of FIGS. 31-33) extend longitudinally, distally from arms 64, respectively.

Figure 22:
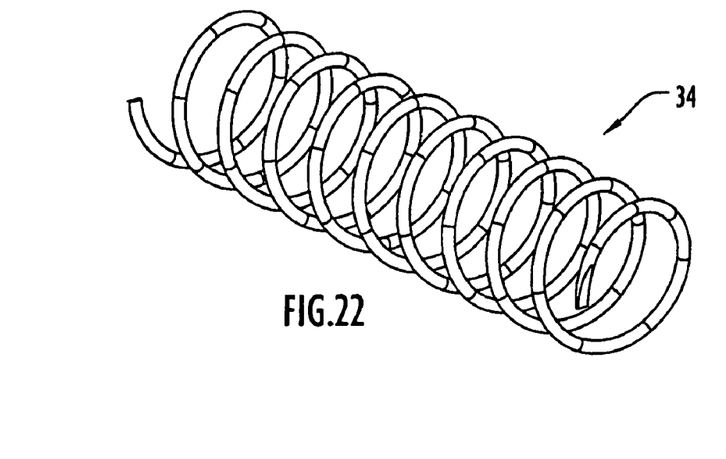
FIG. 22 is a perspective view of a spring for the insertion and extraction tool.
Figure 23:
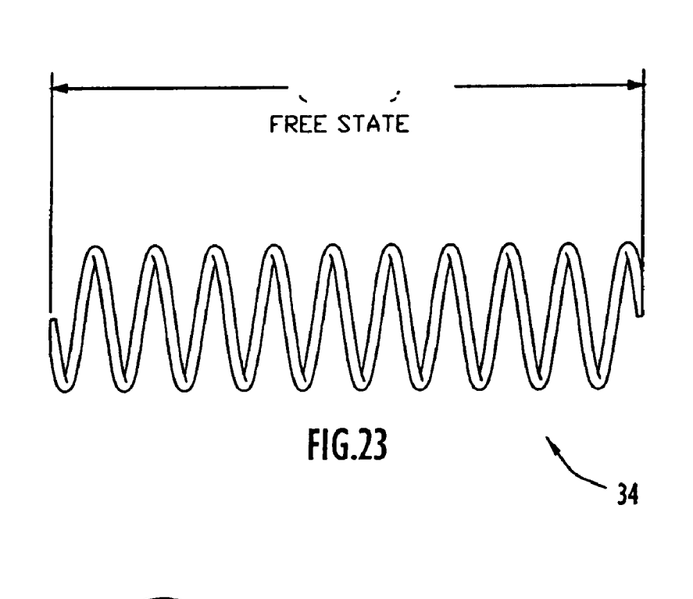
FIG. 23 is a side view of the spring.
Figure 24:
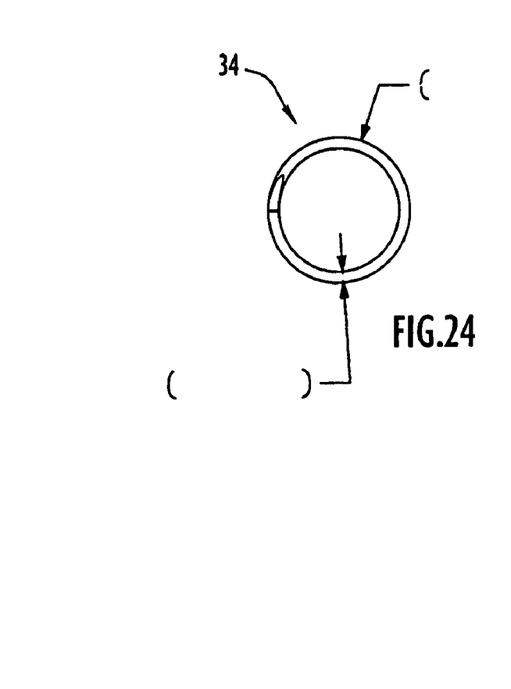
FIG. 24 is an end view of the spring.
Figure 25:
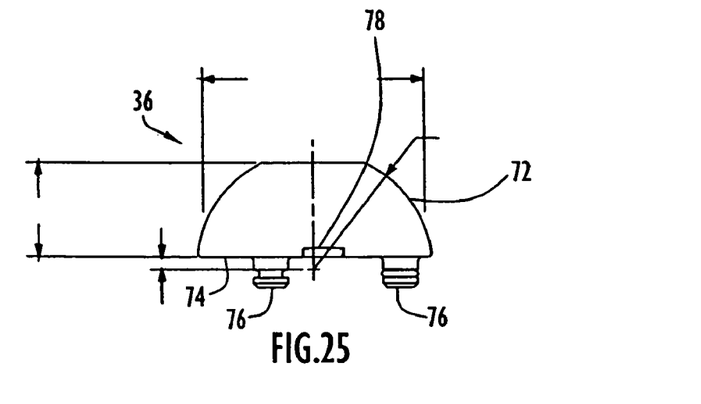
FIG. 25 is a side view of an alignment member for the insertion and extraction tool.
Figure 26:
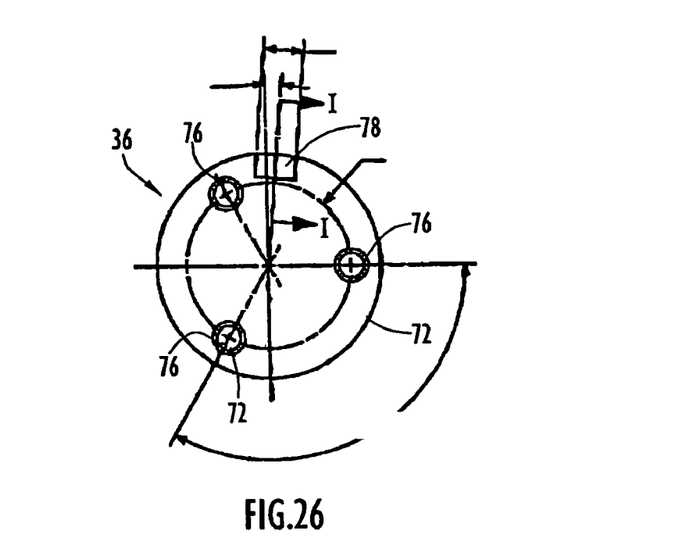
FIG. 26 is an end or top view of the alignment member.
Figure 27:
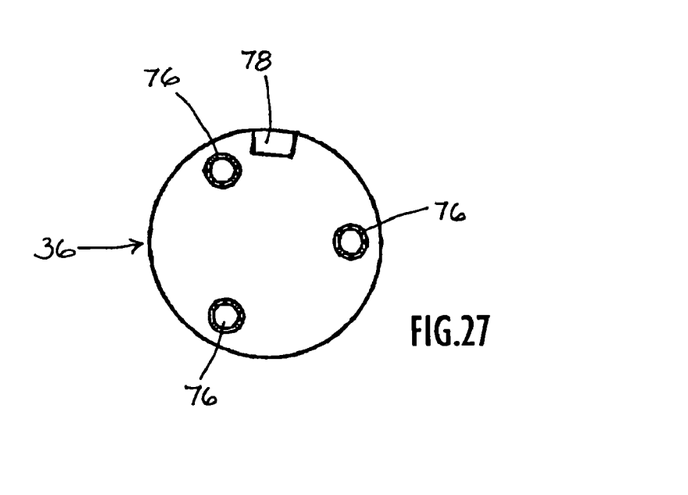
FIG. 27 is an end or top view of the alignment member.
Figure 28:
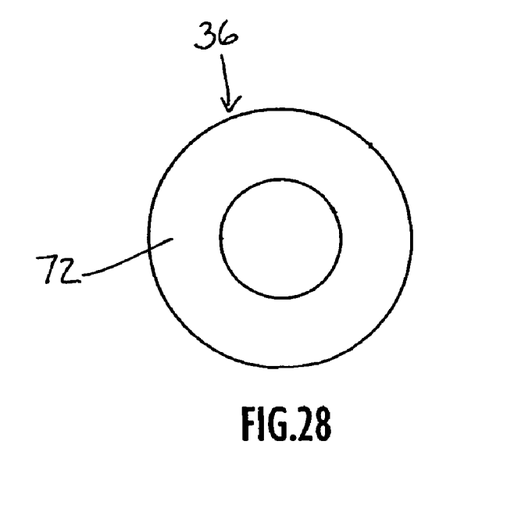
FIG. 28 is an opposite end or bottom view of the alignment member.
Figure 29:
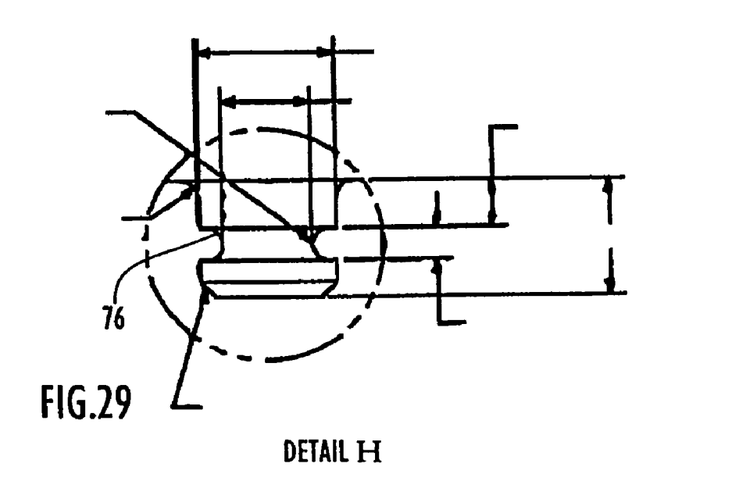
FIG. 29 is an enlarged fragmentary view of detail H of FIG. 25.
Figure 30:
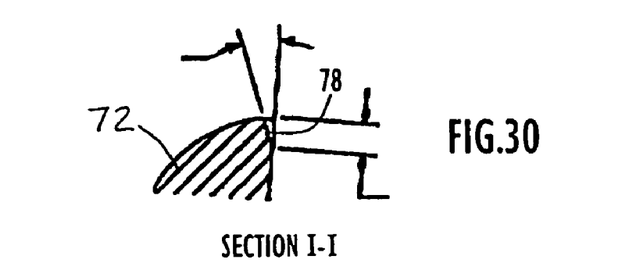
FIG. 30 is an enlarged fragmentary view of section I-I of FIG. 26.
Figure 31:
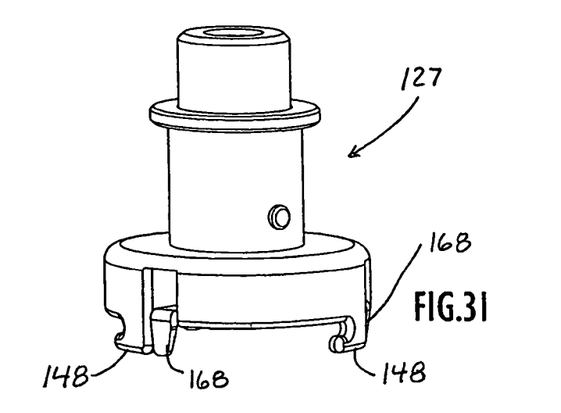
FIG. 31 is a perspective view of an alternative insertion and extraction tool in the locked position.

The spring 34, which is shown in its relaxed state in FIGS. 22-24, is compressed and retained between the proximal end of the stem 60 and the internal ledge 57 of the shaft 42 such that the outer sleeve 37 and the inner shaft 42 are biased longitudinally away from one another such that the locking member 32 is normally disposed in an extended position relative to the engagement plate 44 of engagement member 30 when no actuating force is applied to the tool. In the extended position, the distal end of the outer sleeve 37 abuts the engagement plate 44 and the locking fingers 68 (168 in the embodiment of FIGS. 31-33) are in a longitudinally extended position relative to the engagement plate, in which the fingers 68 (168 in FIGS. 31-33) extend distally beyond the distal face of the engagement plate 44 closely alongside the legs 47 of the engagement protrusions. The distance that the locking fingers 68, 168 extend distally from the distal face of the engagement plate 44 in the extended position may be the same as or substantially the same as the distance between the distal face and the distal edges of feet 48 (designated 148 in FIGS. 31-33). The arms 64 may have distal surfaces disposed in the same plane as the distal face of the engagement plate 44 when the locking member 32 is in the extended position. The extended position for the locking member corresponds to a locked position for the tool and is shown in FIG. 31 for an alternative insertion and extraction tool 127.

Figure 32:
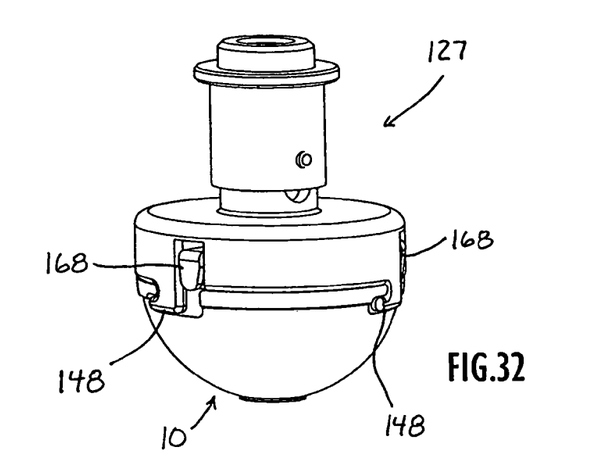
FIG. 32 is a perspective view of the alternative insertion and extraction tool in the unlocked position with the locking fingers of the tool retracted and the engagement protrusions of the tool disposed in the engagement portions of the recesses of the acetabular component.

When an actuating force is applied to the proximal end of the tool to cause relative longitudinal sliding movement of the outer sleeve 37 and the inner shaft 42 away from one another, the locking fingers 68, 168 are retracted within the slots 54 of the engagement plate 44 in a retracted position for the locking member 32 corresponding to an unlocked position for the tool, as shown in FIG. 32 for the alternative tool 127. In the retracted position for the locking member 32, the locking fingers 68 do not protrude distally from the distal face of the engagement plate 44. The actuating force may be applied via manual squeezing operation of the flange 38 of the outer member 28 and the proximal end of inner shaft 42 or via any suitable handle mechanism coupled with the proximal ends of the outer member and the engagement member. When the actuating force is released, the tool is automatically returned to the locked position and the locking member is automatically returned to its extended position since the tool is spring-biased or spring-loaded to the locked position.

The alignment member 36 is shown in FIGS. 25-30 and comprises a generally convex body 72 having a planar end face 74 with bosses 76 protruding therefrom at equally spaced radial locations about a central axis of the alignment member. The bosses 76 have a configuration to be received in the holes 56 in engagement plate 44 to releasably secure the alignment member to the engagement plate. The bosses 76 can be designed in various ways for releasable engagement in holes 56 including a snap fit, an interference fit or any other suitable releasable connection. The body 72 has an external configuration corresponding to the configuration of cavity 16 of the acetabular component 10 to serve as an alignment or centering guide for the insertion and extraction tool 27. An angled notch or recess 78 is formed along the peripheral edge of body 72 to facilitate removal or detachment of the alignment member 36 from the engagement plate 44.

Figure 33:
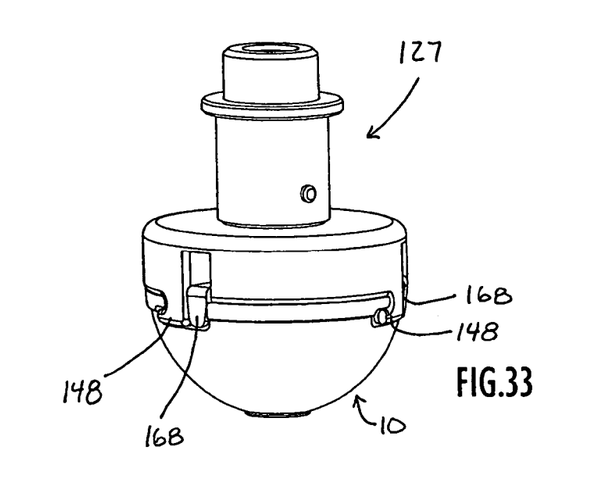
FIG. 33 is a perspective view of the alternative insertion and extraction tool in the locked position with the locking fingers of the tool extended into the recesses to lock the acetabular component to the tool.

A method of locking the acetabular component 10 to the insertion and extraction tool 27 involves moving the insertion and extraction tool from the locked position to the unlocked position in response to an actuating force applied at the proximal end of the tool and moving the tool toward the acetabular cup 10 in an axial or longitudinal direction of movement to align the feet 48 (148 in the embodiment of FIGS. 31-33) with the entry portions 22 of recesses 20. Where the alignment member 36 is provided, this is facilitated by inserting the body 72 into the cavity 16 of the acetabular component and rotating the tool, as needed, about its central longitudinal axis to obtain alignment of the feet 48, 148 with the entry portions 22. Accordingly, the tool is essentially self-guided or self-centered without the surgeon having to engage in trial and error alignment of the feet with the entry portions of the recesses. Continued movement of the tool 27 toward the acetabular component 10 causes the feet 48, 148 to enter and pass through the entry portions 22 into the engagement portions 24 of the recesses 20. The feet 48, 148 will then be disposed in the first ends of the engagement portions 24, with the distal face of the engagement plate 44 in engagement with the face 14 of the acetabular component 10 with the side edges 25 of the engagement portions 24. The insertion and extraction tool 27 is then rotated about its central longitudinal axis in the direction of the second ends of the engagement portions 24, i.e. clockwise for the illustrated embodiment, thusly causing the second ends of the feet 48, 148 to enter the second ends of the engagement portions 24 as represented by FIG. 32. In this position, shoulders 26 are disposed between the feet 48, 148 and the engagement plate 44 to prevent withdrawal of the engagement members 46 from the recesses 20 in the axial or longitudinal direction. The actuating force on the insertion and extraction tool 27 is then removed or released, allowing the tool to return automatically to the locked position, whereby the locking fingers 68, 168 automatically enter the unoccupied portions of the recesses as represented in FIG. 33. An engagement protrusion 46 and a locking finger 68, 168 will be disposed simultaneously in each recess 20 to prevent rotation of the engagement plate 44 relative to the acetabular component 10 about the central longitudinal axis of the tool. In this manner, the acetabular cup 10 will be locked to the insertion and extraction tool 27. In order to unlock the acetabular component 10 from the insertion and extraction tool 27, an actuating force is applied to the proximal end of the tool to move the locking member to its retracted position, causing the locking fingers 68, 168 to be withdrawn from the recesses 20 in the unlocked position for the tool. The tool is then rotated about its central longitudinal axis in the direction of the first ends of the engagement portions 24 of recesses 20, i.e. counterclockwise for the illustrated embodiment, so that the feet 48, 148 are again aligned with the entry portions 22 of the recesses 20. The tool is then moved away from the acetabular component 10 in the axial or longitudinal direction to withdraw the feet 48, 148 from the recesses 20.

When the acetabular component 10 is locked to the insertion and extraction tool 27, the acetabular component can be adjustably positioned as needed in the cavity prepared in the bone to receive the acetabular component as accomplished via manipulation of the proximal end of the tool. Impaction forces may be applied to the tool 27 in order to insert the acetabular component 10 in the bone cavity, and the tool will remain locked to the acetabular cup even where vigorous impaction forces are applied. The engagement protrusions and locking fingers, when disposed in the recesses of the acetabular component, essentially complete the partial spherical configuration of the outer surface of the acetabular component and do not interfere with insertion of the acetabular component in the bone cavity. Once the acetabular component 10 has been inserted in the bone cavity, the tool is moved to the unlocked position for withdrawal from the acetabular component. The tool may also be used for extraction of an implanted acetabular component by locking the tool to the implanted acetabular component and then applying the necessary extraction force to disengage the acetabular component from the bone cavity. The tool can then be withdrawn from the patient's body carrying the acetabular component therewith. Regardless of whether the tool is used for insertion or extraction, the tool is automatically self-locking to the acetabular component in response to relative longitudinal movement of the locking member and the engagement plate that occurs automatically when the tool returns to the locked position upon release of the actuating force.

What is claimed is:

1. An acetabular component and an insertion and extraction tool for use with the acetabular component, comprising
an acetabular component comprising a partial spherical body having
a peripheral surface circumscribing a cavity,
a plurality of recesses along an outer surface of said body each having an entry portion along said peripheral surface leading into an engagement portion angled from said entry portion,
each of said engagement portions having a first end aligned with said entry portion and a second end extending beyond said entry portion to define a shoulder between said second end and said peripheral surface; and
an insertion and extraction tool comprising an outer sleeve having a distal end carrying
a locking member including a plurality of radially extending arms and a locking finger extending distally from each of said arms,
an inner shaft, slidably disposed in said outer sleeve and having a distal end carrying an engagement plate disposed distally of said distal end of said outer sleeve and having a plurality of engagement protrusions, each of said engagement protrusions including a leg extending distally from said engagement plate to a foot angled from said leg,
said engagement plate having a plurality of channels therein slidably receiving said arms, respectively, and
a spring biasing said outer sleeve and said shaft longitudinally to a locked position for said tool in which said locking member is in an extended position relative to said engagement plate wherein said locking fingers protrude distally beyond said engagement plate alongside said legs of said engagement protrusions,
said tool being movable to an unlocked position in response to an actuating force applied to said tool to effect relative longitudinal movement of said outer sleeve and said shaft to move said locking member to a retracted position relative to said engagement plate wherein said locking fingers are retracted within said channels,
said feet being insertable through said entry portions into said first ends of said engagement portions of said recesses with said tool in said unlocked position and being movable into said second ends of said engagement portions in response to rotation of said engagement plate about its central longitudinal axis,
said shoulders preventing withdrawal of said engagement protrusions from said recesses in a longitudinal direction and
said recesses presenting portions unoccupied by said engagement protrusions when said feet are moved into said second ends of said engagement portions,
said tool being returned automatically to said locked position by said spring in response to removal of the actuating force to cause said locking fingers to enter said unoccupied portions and prevent rotation of said engagement plate about its central longitudinal axis whereby said acetabular component is locked to said tool.

2. The acetabular component and the insertion and extraction tool as recited in claim 1 and further comprising an alignment member disposed on said engagement plate for insertion in said cavity of said acetabular component to facilitate alignment of said feet with said entry portions of said recesses.

3. The acetabular component and the insertion and extraction tool as recited in claim 1, further comprising at least one of said locking fingers having a tapered edge portion, said tapered edge portion serving to securely wedge said locking finger between said foot and a wall of said recess.

4. The acetabular component and the insertion and extraction tool as recited in claim 3, wherein an opposing edge of said at least one locking finger is a straight edge.

5. The acetabular component and the insertion and extraction tool as recited in claim 4, wherein said straight edge of said at least one locking finger slidingly abuts a straight edge of an adjacent foot member.

6. The acetabular component and the insertion and extraction tool as recited in claim 5 and further comprising an alignment member disposed on said engagement plate for insertion in said cavity of said acetabular component to facilitate alignment of said feet with said entry portions of said recesses.

7. The acetabular component and the insertion and extraction tool as recited in claim 5, wherein said outer surface of said acetabular component is configured for attachment to acetabular bone.

8. The acetabular component for releasable engagement with locking structure of an insertion and extraction tool as recited in claim 3, wherein said acetabular component has three said recesses.

9. The acetabular component and the insertion and extraction tool as recited in claim 3, wherein said outer surface of said acetabular component is configured for attachment to acetabular bone.

10. The acetabular component and the insertion and extraction tool as recited in claim 9, wherein said outer surface comprises a porous or rough coating configured to promote bone in-growth or on-growth.

11. The acetabular component for releasable engagement with locking structure of an insertion and extraction tool as recited in claim 1, wherein said acetabular component has three said recesses.

12. The acetabular component and the insertion and extraction tool as recited in claim 1, wherein said outer surface of said acetabular component is configured for attachment to acetabular bone.

13. The acetabular component and the insertion and extraction tool as recited in claim 12, wherein said outer surface comprises a porous or rough coating configured to promote bone in-growth or on-growth.

14. An acetabular component for releasable engagement with locking structure of an insertion and extraction tool as recited in claim 12, wherein said acetabular component has three said recesses.

* * * * *